(12) United States Patent
Schöb et al.

(10) Patent No.: US 6,640,617 B2
(45) Date of Patent: Nov. 4, 2003

(54) APPARATUS AND A METHOD FOR DETERMINING THE VISCOSITY OF A FLUID

(75) Inventors: Reto Schöb, Volketswil (CH); Simon Huwyler, Oberägeri (CH)

(73) Assignee: Levitronix LLC, Waltham, MA (US)

( * ) Notice: Subject to any disclaimer, the term of this patent is extended or adjusted under 35 U.S.C. 154(b) by 0 days.

(21) Appl. No.: 10/162,811

(22) Filed: Jun. 4, 2002

(65) Prior Publication Data

US 2003/0033859 A1 Feb. 20, 2003

(30) Foreign Application Priority Data

Aug. 16, 2001 (EP) .............................. 01810790
Dec. 4, 2001 (EP) .............................. 01811173

(51) Int. Cl.[7] .............................................. G01N 11/14
(52) U.S. Cl. ...................................... 73/54.01; 73/54.28
(58) Field of Search ........................... 73/54.28, 54.01; 123/381; 239/75; 137/92; 366/151.1, 152.3, 152.5; 62/135, 136; 188/276, 266, 327.5

(56) References Cited

U.S. PATENT DOCUMENTS

| | | | |
|---|---|---|---|
| 4,299,119 A | * 11/1981 | Fitzgerald et al. | 73/54.28 |
| 4,643,021 A | 2/1987 | Mattout | 73/54.28 |
| 5,307,288 A | 4/1994 | Haines | 702/47 |
| 5,353,827 A | * 10/1994 | Bouchard et al. | 137/1 |
| 5,798,454 A | 8/1998 | Nakazcki et al. | 73/54.28 |
| 6,100,618 A | 8/2000 | Schoeb et al. | 310/90.5 |
| 6,149,508 A | 11/2000 | Vanell et al. | 451/72 |
| 6,167,752 B1 | * 1/2001 | Raffer | 73/54.28 |
| 6,241,485 B1 | 6/2001 | Warwick | 417/300 |

FOREIGN PATENT DOCUMENTS

| | | | |
|---|---|---|---|
| DE | 4243118 A1 | 6/1994 | F04D/15/00 |
| EP | 0967475 A1 | 12/1999 | A61H/1/10 |
| JP | 09137792 | 5/1997 | F04D/13/02 |

* cited by examiner

Primary Examiner—Hezron Williams
Assistant Examiner—David Rogers
(74) Attorney, Agent, or Firm—Townsend and Townsend and Crew LLP

(57) ABSTRACT

An apparatus and a method for determining the viscosity of a fluid includes an electrical rotary drive (2) with a stator (3), which has a stator winding (4), and with a rotational body (5) which can rotate in the fluid (1). The rotational body (5) is designed as a rotor (5) of the rotary drive (2) and is magnetically journalled in a contact-free manner with respect to the stator (3).

27 Claims, 9 Drawing Sheets

APPARATUS AND A METHOD FOR DETERMINING THE VISCOSITY OF A FLUID

BACKGROUND OF THE INVENTION

The invention relates to an apparatus and to a method for determining the viscosity of a fluid.

Newton's law of friction describes the intensity of the internal friction between adjacent layers in a flowing fluid for the simple case of a laminar flow as, for example, in a flowing liquid or in a gas. The internal friction force $F_R$, which acts on such a layer in the flowing fluid, is proportional to its area A and to a velocity gradient dv/dx (v: velocity of the flowing fluid at the location x) with respect to an adjacent layer of the same area. In the case of a laminar flow, the well-known simple relationship applies of $F_R = \eta \cdot A \cdot dv/dx$, where the dynamic viscosity $\eta$ is to be seen as a measure for the viscosity of the fluid. In addition to the correct SI unit Pa·s for the dynamic viscosity, the unit 1 poise=0.1 Pa·s is still very common. In addition to the dynamic viscosity $\eta$, the so-called kinematic viscosity $v=\eta/\rho$ ($\rho$: density of the fluid) normed to the density of the fluid represents an important characteristic of a fluid. Within the framework of this application, viscosity is always to be understood as the "dynamic viscosity $\eta$" following usual language use.

As the above statements show, the viscosity can generally be determined by a measurement of the internal friction $F_R$ of the fluid. For this purpose, a sample of known geometry is moved in a static or flowing fluid, with a measurable proportion of the driving power of the sample being converted into heat as power loss due to the internal friction $F_R$ in the fluid. Ultimately, the viscosity $\eta$ and/or the kinematic viscosity v can be determined from the measured power loss, possibly while taking into account further parameters such as geometric factors or further calibration parameters.

In practice, a sample of known geometry is rotated in a static or flowing fluid by means of an electrical drive and the viscosity $\eta$ is determined from the measured electrical power loss of the drive. The specific shape of the sample can be taken into account, for example, by calibration measurements on fluids of well-known viscosity. It must furthermore be taken into account that the viscosity is also dependent on physical state quantities such as on the temperature or on the pressure of the fluid and is generally to be considered as a function of further physical characteristics such as the density.

Viscosimeters, which work while taking into account the above constraints and in accordance with the previously described principles or according to related principles, have long been known in a number of different variants. In order to be able to determine the viscosity of the fluid from the electrical power taken up by the rotary drive of the viscosimeter, that proportion of the total power loss must be known as accurately as possible which is due solely to the internal friction in the liquid. This means in particular that all friction losses which occur for example in bearings of the rotary drive themselves or at seals of feedthroughs of drive rods, etc., must be known very precisely. Particularly these parameters are, however, as a rule not sufficiently known in conventional electrical drive systems for viscosimeters. Furthermore, the previously mentioned, unwanted additional friction losses can depend on the current operating parameters under which the viscosimeter has to be operated, such as on the temperature or on the density of the fluid to be investigated and even on the actual viscosity to be investigated (low or high viscosity, gas or liquid). For this reason, the measuring precision of known viscosimeters is frequently unsatisfactory, or a substantial additional effort must be made to calibrate the measuring arrangement, with the calibration having to be made again each time for a change in the operating parameters and/or the conversion of the measurement to a fluid with different physical characteristics. This circumstance in particular impedes or hinders a precise determination of the viscosity when this changes in the course of the measurement, i.e. when the viscosity of a process is to be determined "in-line". For instance, the time development of slow chemical reactions (in the liquid or gaseous milieu) in a reaction vessel, for example, can very frequently only be observed with insufficient precision by a time-dependent measurement of the viscosity with the known viscosimeters. The viscosity within an inhomogeneous fluid can also depend greatly on the place. For instance, the mixing of the fluid in a reaction vessel could, for example, basically be controlled via the viscosity, which is, however, only possible with the known viscosimeters with a great effort and/or the tolerating of massive measuring errors.

Special problems can occur if the viscosity of chemically or physically aggressive fluids is to be determined. For instance, with special liquids, which contain solid particles for example, substantial damage can occur at sealing components due to abrasion, for example at feedthrough seals of the drive rods. The same applies to chemically aggressive liquids such as acids or lyes which can permanently damage the sealing rings of drive components.

In practice, numerous processes and methods can be found in which the constant monitoring of the viscosity $\eta$ can play an important role. For example, a layer of photo-resist of a well-defined thickness has to be applied to a wafer in the production of integrated circuits. Usually, for this purpose, the wafer is set into fast rotation with a defined speed and the photo-resist is applied to the rotating wafer via a feed device. In this connection, the larger part of the applied photo-resist is slung off due to the rotation of the wafer. The resulting layer thickness on the wafer is substantially greatly dependent, among other things, on the viscosity $\eta$ of the photo-resist to be applied. It would therefore be of advantage to continuously control the viscosity $\eta$ of the photo-resist before application and possibly to correct it by mixing in one or more additional components; i.e. the viscosity $\eta$ should be monitored in-line and with high precision. A further important example to be named is that of chemical-physical polishing processes, so-called CMP processes (chemical-mechanical polishing), which likewise enjoy wide application in the semi-conductor industry. In such processes, a suspension known as a slurry is usually used as the polishing liquid which contains very fine solid particles whose uniform distribution in the suspension can be monitored especially simply by a measurement of the viscosity $\eta$.

SUMMARY OF THE INVENTION

It is therefore an object of the invention to provide another apparatus for measuring the viscosity of a fluid by means of a rotating sample which allows the most accurate determination possible of the viscosity, in particular also in-line, that is, in the course of the process. Furthermore, a method should be provided for operating such an apparatus.

In accordance with the invention, an apparatus and a method are provided for determining the viscosity of a fluid, with the apparatus including an electrical rotary drive having a stator with a stator winding and with a rotational body rotatable in the fluid. The rotational body is designed as a rotor of the rotary drive and magnetically journalled in a contact-free manner with respect to the stator.

It is important for the invention that the drive of the rotational body is not connected with any friction losses in the form of bearing friction or similar. This is achieved in that the rotational body, which is designed as a rotor of the electrical rotary drive of the apparatus in accordance with the invention, is magnetically journalled in a contact-free manner with respect to the stator. The rotor is thus mechanically completely uncoupled from the other components of the rotary drive. The electrical driving power to be applied for the rotation of the sample in the fluid thus substantially depends only on the viscosity of the fluid and is not also determined by additional losses. If no hydraulic pump performance at all is provided by the rotational body in operation, the torque forming current of the rotary drive in static operation is determined—with the exception of negligible ohmic loss—only by the internal friction of the fluid in which the rotational body rotates, that is, solely by the viscosity of the fluid.

The electrical rotary drive for the apparatus in accordance with the invention for determining the viscosity of a fluid is preferably designed in accordance with EP 0 819 330 or EP 1 063 753 as a bearing-free motor with a magnetically journalled rotor and a stator, with the drive and the magnetic support for the rotor forming a unit in accordance with the principle of a bearing-free motor. The stator has a drive winding with a strand for generating a magnetic drive field which produces a torque on the rotor. The magnetic drive field is in this connection controlled by a torque forming current. In addition, the stator has a control winding including at least one strand for generating a magnetic control field with which the position of the rotor with respect to the stator can be regulated via a control current. The magnetic drive field and the magnetic control field can be completely uncoupled from one another so that the torque forming current of the drive winding feeds the total mechanical motor power on its own. The total mechanical motor power which has to be applied on the operation of the bearing-free motor as the rotary drive of the apparatus in accordance with the invention results as the sum of viscous power loss caused by the rotation of the rotational body in a fluid and a possibly simultaneously supplied pump power by pumping the fluid against a pressure difference. In this connection, the pump power results simply by multiplication of the pumped flow by the corresponding pressure difference, while the mechanical motor power is proportional to the product of torque forming current and rotational frequency of the rotational body in the fluid. With a known hydraulic pump power, the viscous power loss can thus be determined directly from the torque forming current and the rotational frequency of the rotational body and from this the viscosity $\eta$ of the fluid. In particular with a very small or negligible hydraulic pump power, the viscosity $\eta$ of the fluid is thus directly proportional to the torque forming current with a given constant rotational frequency.

The invention will be explained in more detail in the following with reference to the schematic drawing.

DESCRIPTION OF THE PREFERRED EMBODIMENTS

Figure 1:
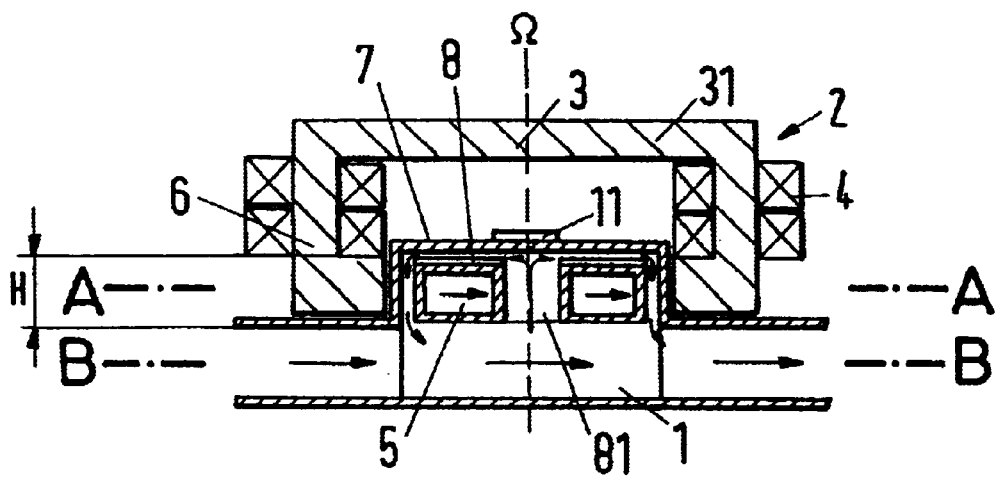
FIG. 1 shows an embodiment of an apparatus in accordance with the invention including a temple motor (see WO 98/11650, FIG. 8k) with a stator, a stator winding, a rotational body and a rotor housing.

FIG. 1 shows in a schematic illustration an embodiment of an apparatus in accordance with the invention for determining the viscosity $\eta$ of a fluid 1. The apparatus includes an electrical rotary drive 2 having a stator 3 and a rotational body 5 rotatable in the fluid 1 which is designed as the rotor 5 of the rotary drive 2. The diameter D of the rotor 5 is preferably larger than its height H extending in the axial direction. In this connection, it is important for the invention that the rotational body 5 is magnetically journalled in a contact-free manner with respect to the stator, with no separate magnetic bearings being present for the rotor 5. The stator 3 of the electrical rotary drive 2 has a stator winding 4 which includes a drive winding for generating a magnetic drive field and a control winding for generating a magnetic control field with which the position of the rotor 5 with respect to the stator 3 can be regulated via a control current. Furthermore, the stator winding 4 can include yet a further winding for generating a heating current. The magnetic drive field, which is suitable to produce a magnetic rotational field, exerts a torque on the rotor 5 and sets the rotational body 5 into rotation with respect to the stator 3. The magnetic rotational field can in this connection be controlled by a torque forming current $I_q$ in accordance with the known method of the field-oriented drive regulation (known in English as "vector control").

If, within the framework of this application, the term of electrical current is used as an electrical state parameter or control parameter, this term naturally also stands for other electrical parameters such as electrical voltage or power which are suitable for characterization in an analogous manner.

Figure 2:
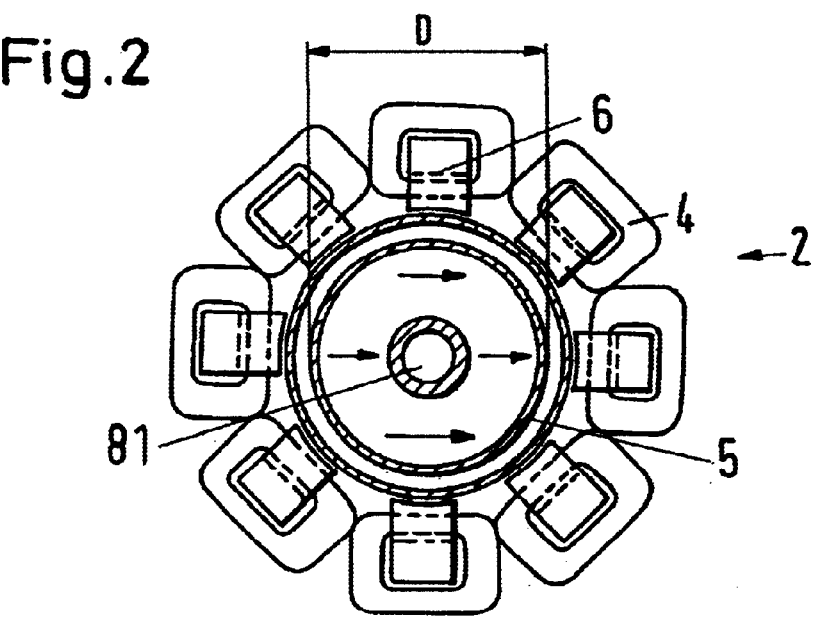
FIG. 2 is a section through the rotor housing in accordance with FIG. 1 along the line A—A.

The rotary drive 2 is preferably designed as a temple motor in which the stator 3 includes a plurality of stator teeth 6 connected by a magnetic return yoke 31 which have a longer and a shorter limb and are each formed in an L shape. In this connection, the longer limb preferably extends parallel to the desired axis of rotation $\Omega$ of the rotor 5 and the shorter limb extends radially in the direction of the desired axis of rotation $\Omega$. The shorter limbs of the plurality of stator teeth 6 in this connection form, as shown in FIG. 2, a substantially cylindrical region which is suitable to receive the rotational body 5. The rotor 5 is preferably permanently magnetic, but can naturally also be designed as a field-stimulated rotor 5. A particular advantage of the permanently magnetically stimulated rotor 5 in comparison with the field-stimulated rotor 5 lies in the fact that no current and thus no energy is required for the field stimulation. The use of a rotary drive 2 having a permanently magnetically stimulated rotor 5 therefore proves to be especially advantageous for determining the viscosity $\eta$ by measuring the torque forming current $I_q$. The rotational body 5 can be fully or partly enclosed by a rotor housing 7. However, it is quite conceivable that, under certain circumstances, the rotational body 5 is not received in a rotor housing 7. For instance, if corresponding electrical insulation measures have been taken, the apparatus in accordance with the invention can be located fully or partly within the fluid 1, for example in a container filled with the fluid 1 so that a rotor housing 7 is superfluous.

Figure 3:
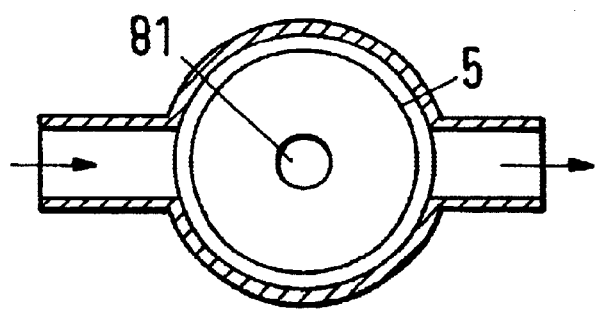
FIG. 3 is a section through the rotor housing in accordance with FIG. 1 along the line B—B.
Figure 4:
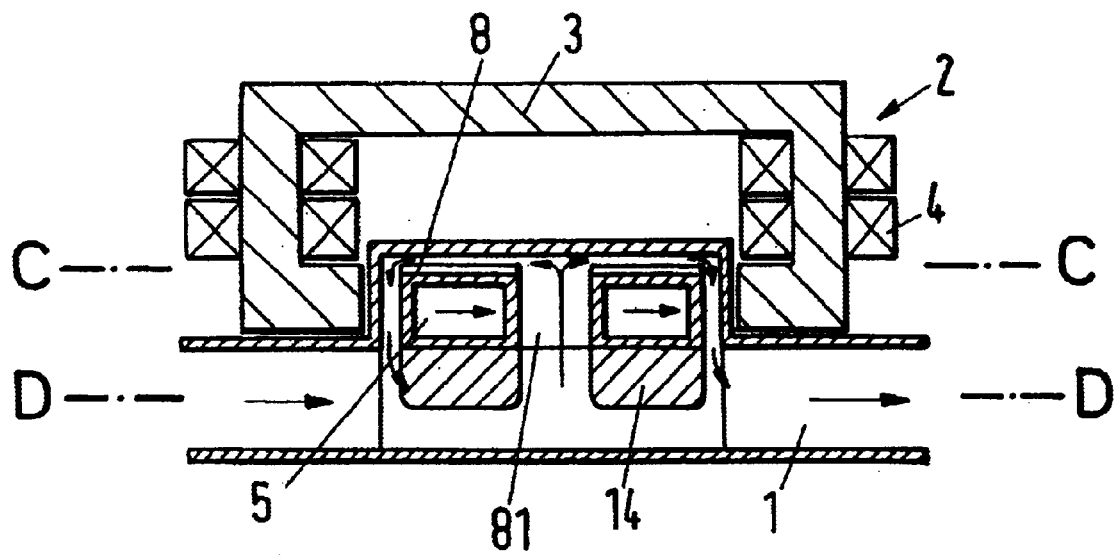
FIG. 4 shows a second embodiment of an apparatus in accordance with the invention with a circulation aid.
Figure 6:
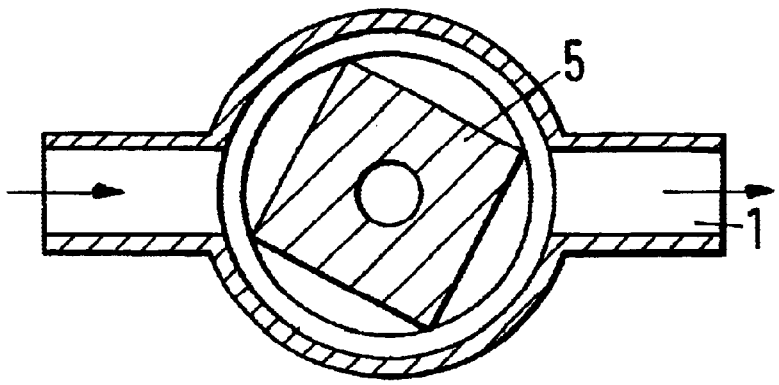
FIG. 6 shows an embodiment for a special form of the rotational body.
Figure 4A:
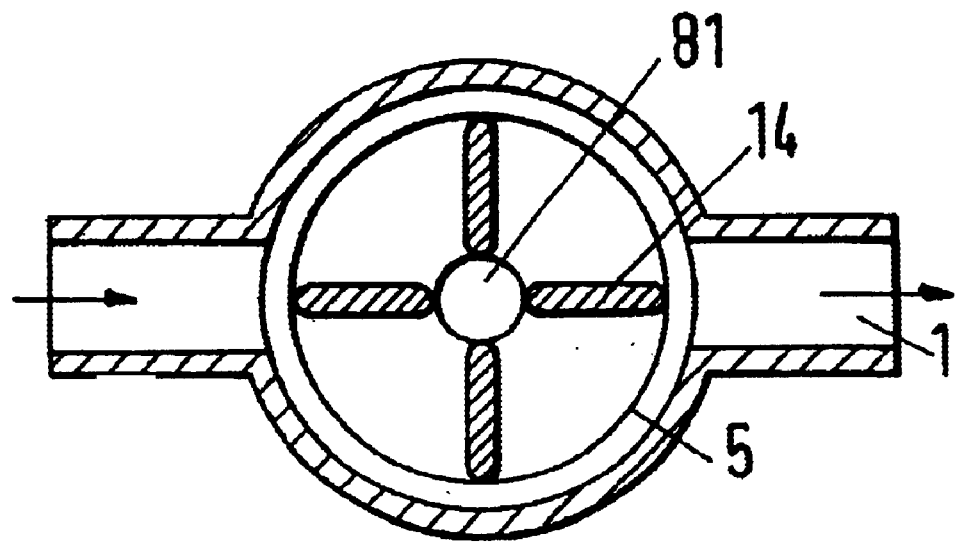
FIG. 4a is a section through the embodiment of a device 14 in accordance with FIG. 4 along the line D—D.
Figure 5:
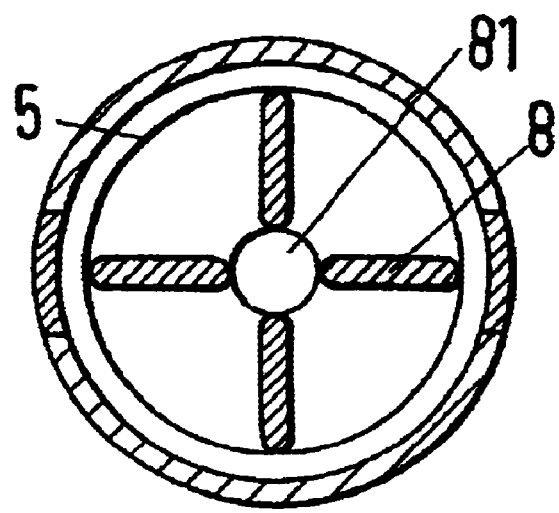
FIG. 5 is a section through the embodiment for a circulation aid in accordance with FIG. 4 along the line C—C.

In a particularly simple embodiment, the rotational body 5 is formed as a flat disk with substantially smooth surfaces. Driven by the magnetic rotational field, the rotational body 5 rotates in the fluid 1, with the torque forming current $I_q$ being substantially determined solely by the viscosity $\eta$ of the fluid 1 in the static state, i.e. when the rotary drive 2 has achieved a constant speed $\omega$. Since, in particular for measurements in the course of a process, with so-called in-line measures, the value of the viscosity $\eta$ can fluctuate spatially and/or temporally, care must be taken that a sufficient circulation of the fluid 1 is ensured. If, for example, as indicated in FIG. 1, the viscosity $\eta$ of a flowing fluid 1 should be monitored continuously, it must be ensured by suitable measures that new fluid 1 constantly flows around the rotational body 5. For this purpose, the rotational body 5 can include a circulation aid 8 which, in the simplest case as shown, for example, in FIG. 1 and FIG. 3, can be realized by one or more drillings 81 in the radial and/or axial direction. A shovel-like device is preferably present as a circulation aid 8 at a surface of the rotational body 5, as shown in FIG. 5. Differently designed structural elements, which improve the circulation of the fluid 1 as a circulation aid 8 at the rotor 5 or also at the rotor housing 7, are also quite conceivable. A suitable choice of the shape of the rotational body can also improve the circulation of the fluid 1, as FIG. 6 shows. A combination of different circulation aids 8 is naturally also conceivable. In this connection, the structuring properties of the circulation aid 8 can also contribute to increasing the measuring accuracy of the apparatus in accordance with the invention, since the friction of the rotational body 5 in the fluid 1 is generally increased by the circulation aid 8, which in particular increases the fluctuations in the torque forming current $I_q$ and thus the measuring sensitivity with a fluctuating viscosity $\eta$. As shown schematically in FIG. 4 and FIG. 7, to increase the measuring sensitivity, further devices 14 can be present, which are suitable to couple additional masses of fluid 1 to the rotational body 5 and thus to increase the flow resistance of the rotational body in the fluid 1. The devices 14 prove to be particularly advantageous with low viscosity fluids 1 or with fluids 1 of low density. FIG. 4a shows an embodiment of the devices 14 in accordance with FIG. 4 in section along the line D—D.

Figure 9:
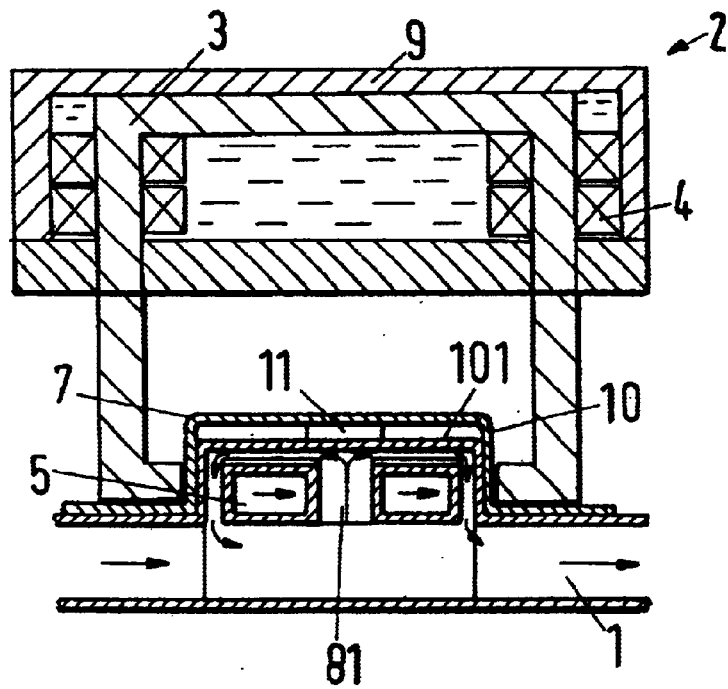
FIG. 9 shows a fourth embodiment in accordance with FIG. 1, with means for heat isolation being provided.

In addition to different measuring probes, e.g. for determining the thermodynamic state parameters such as the pressure which prevails in the fluid 1 or measuring probes for measuring different chemical or physical characteristics of the fluid 1 such as pH sensors or optical sensors, the apparatus in accordance with the invention can also have a temperature sensor 11 (FIG. 1) for determining the temperature T of the fluid 1. With a plurality of fluids 1, the viscosity $\eta$ namely depends more or less strongly on the temperature T so that the temperature T has to be determined simultaneously with and at the same location as the viscosity $\eta$. Under certain circumstances, it can be necessary for the apparatus in accordance with the invention, which naturally produces a certain amount of ohmic heat in the stator winding 2, to be thermally largely uncoupled from the fluid 1. Different measures are conceivable for this purpose, of which individual ones will be explained by way of example in the following. As shown in FIG. 9, for example, the longer and/or the shorter limbs of the stator teeth 6 of an L-shape can be designed such that the region of the stator 3 including the stator winding 4 is arranged with respect to the rotational body 5 such that a maximum of 50%, preferably at most 5%, of the thermal power of the stator winding 4 can be coupled into the fluid 1. A thermal uncoupling of fluid 1 and stator winding 4 can, however, also be achieved, for example, by means for heat insulation. For instance, as shown in FIG. 9, both the stator 3 of the rotary drive 2 can have an insulation means 9 for the heat insulation and likewise the rotor housing 7 can include a device 10 for the heat insulation. The insulation means 9 can be designed, for example, as a cooling jacket which includes a housing with cooling ribs, said housing being able to be additionally externally cooled and/or comprising further devices for the dissipation of heat. The device 10 for heat insulation of the rotor housing 7 can, as shown in FIG. 9, be designed as a casing such that an intermediate space 101 is formed between the device 10 and the rotor housing 7 which is suitable for receiving the temperature sensor 11 and for receiving heat insulating materials. It is also conceivable that the intermediate space 101 is evacuable, whereby a particularly effective heat insulation can be achieved. The device 10, just like the insulation means 9, can naturally also be designed as a cooling jacket which includes a housing with cooling ribs, said housing being able to be additionally externally cooled and/or comprising further devices for the dissipation of heat.

A thermal uncoupling of stator winding 4 and fluid 1 is, however, not desirable in every case. Frequently, the temperature dependent viscosity $\eta$ must be determined at one or more defined temperatures T; i.e. the temperature T of the fluid must be able to be controlled and/or regulated. In such a case, the apparatus in accordance with the invention can also be used to thermostat the fluid 1, i.e. simultaneously as a heating. For this purpose, a heating current which can be adjustable in its amplitude and its frequency can be applied to one of the windings of the stator 3, whereby the stator 3 and thus the fluid 1 can be brought to a pre-settable temperature T by thermal coupling to the stator teeth 6. For generating the heating current, the stator winding 4 can also include an additional separate heating coil. Alternatively, in a field-oriented regulation of the drive, in addition to the torque forming current $I_q$, a magnetization current can be applied which, in particular in the case of a permanently magnetically stimulated drive 2, primarily effects an increase in the losses in the stator winding 4 and thus allows a regulation of the temperature T.

Figure 7:
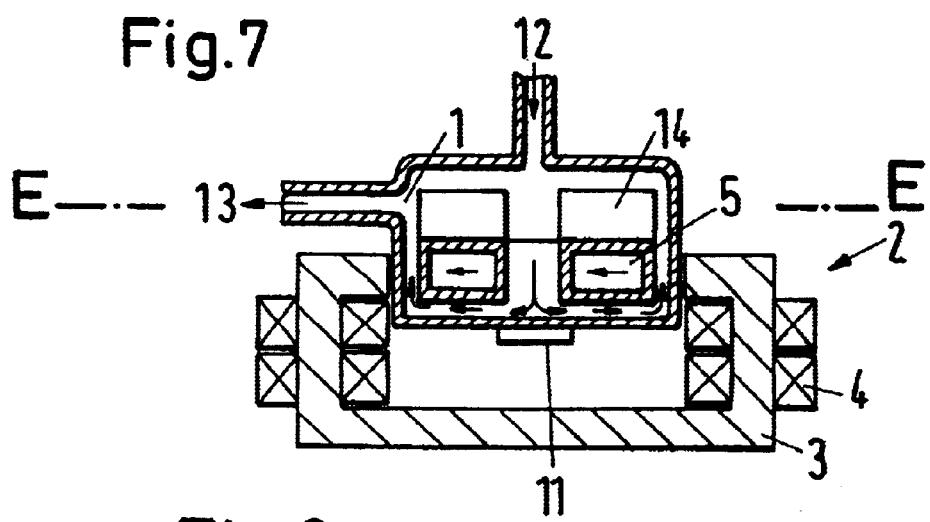
FIG. 7 shows a third embodiment with a centrifugal pump, with the rotational body being completely surrounded by a rotor housing.
Figure 8:
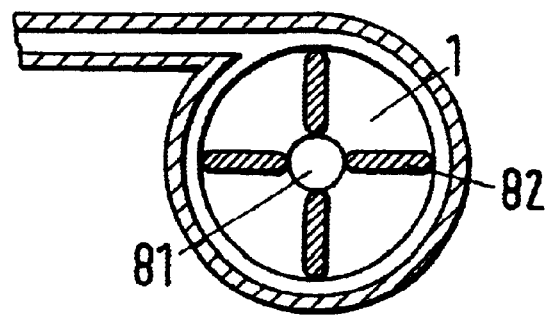
FIG. 8 is a section through the embodiment in accordance with FIG. 7 along the line E—E.
Figure 7A:
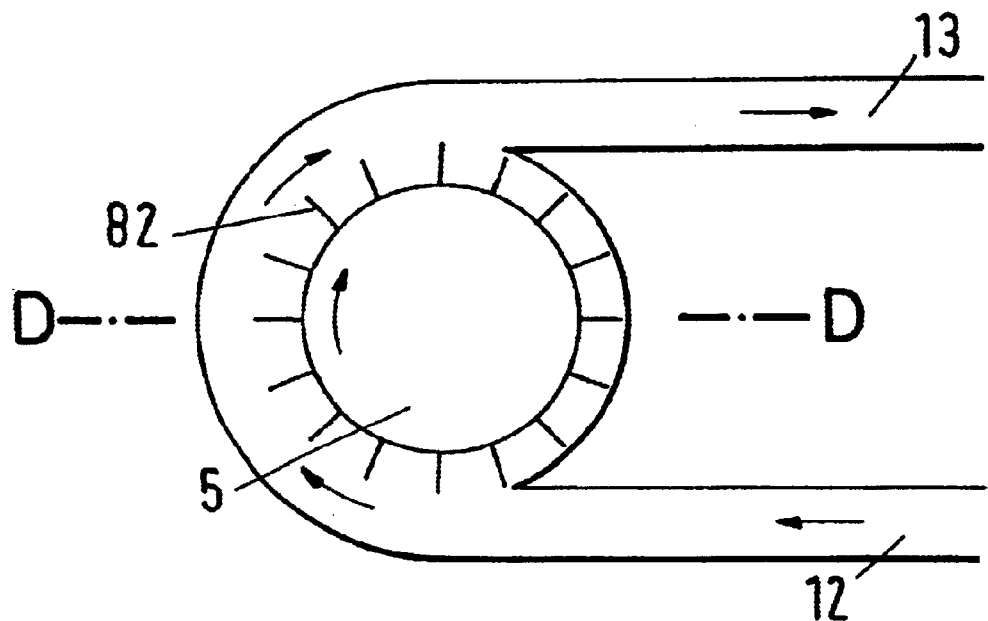
FIG. 7a shows a further embodiment as in FIG. 7, designed as a side passage pump.
Figure 7B:
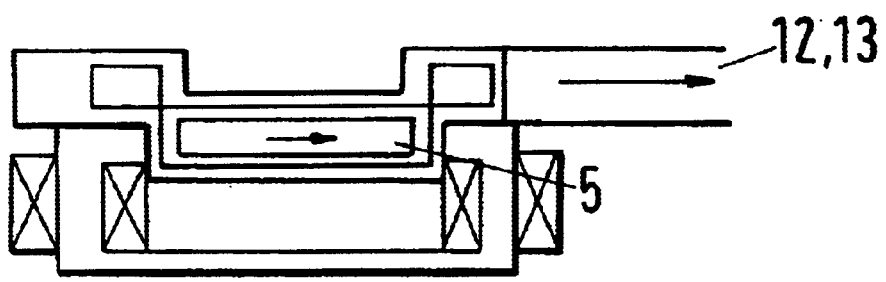
FIG. 7b is a section through the embodiment in accordance with FIG. 7a along the line D—D.
Figure 15:
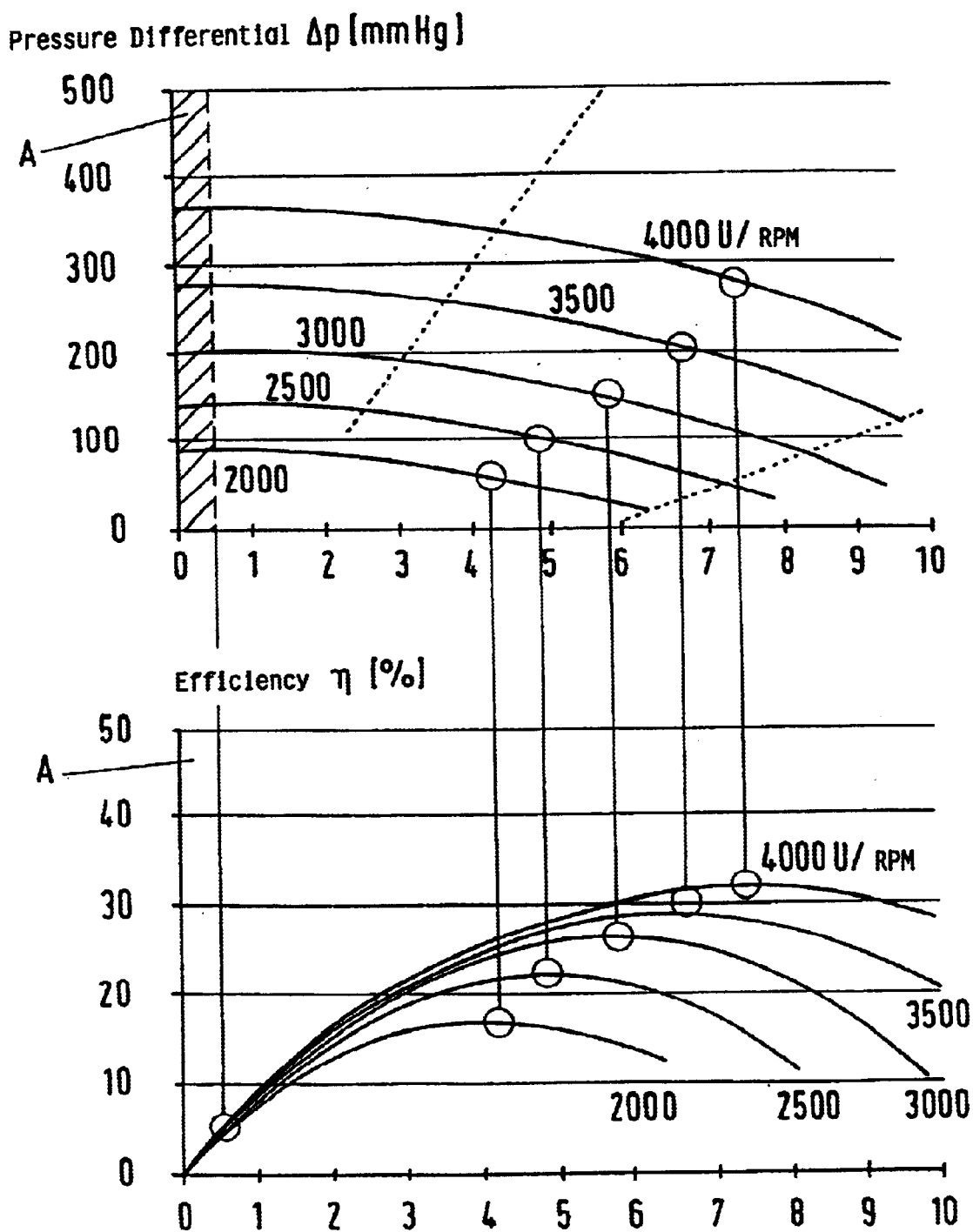
FIG. 15 is a representation of a relationship between the pressure difference (top) and efficiency (bottom) in a rotary pump.

It can be achieved by a suitable arrangement and formation of the rotational body 5 that the rotating rotational body 5 additionally supplies an adjustable hydraulic pump power. In this connection, the rotary drive 2, as shown by way of example in FIG. 15, is preferably operated in an operating range A, in which the portion of the viscose power loss which is converted in the fluid by the rotation of the rotational body 5 amounts to at least 80% of the mechanical power of the electrical rotary drive 2, in particular at least 95%. When determining the viscosity η from the torque forming current $I_q$, the hydraulic pump power naturally has to be taken into account which results as the product of the pumped volume flow with the corresponding pressure difference Δp. If the apparatus in accordance with the invention is operated, as described above, in the operating range A, the volume pumped per time unit is directly proportional to the rotational frequency ω of the rotary drive 2 and thus particularly easy to determine, unless the hydraulic pump power is negligibly small in comparison with the viscose power loss. FIGS. 7 and 7a show by way of example one embodiment each of the apparatus in accordance with the invention which are suitable to supply a hydraulic pump power. The embodiment in FIG. 7 shows a centrifugal pump schematically in which the rotational body 5 is completely surrounded by the rotor housing 7. The rotor housing 7 here includes an inflow 12 to deliver the fluid 1 and an outflow 13 to drain the fluid 1. FIG. 7a shows a side passage pump schematically as another variant of such an embodiment. FIGS. 7b and 8 each show a section along the line D—D in accordance with FIG. 7a or along the line E—E in accordance with FIG. 7 with pump vanes 82 to generate a hydraulic pump power.

Figure 10:
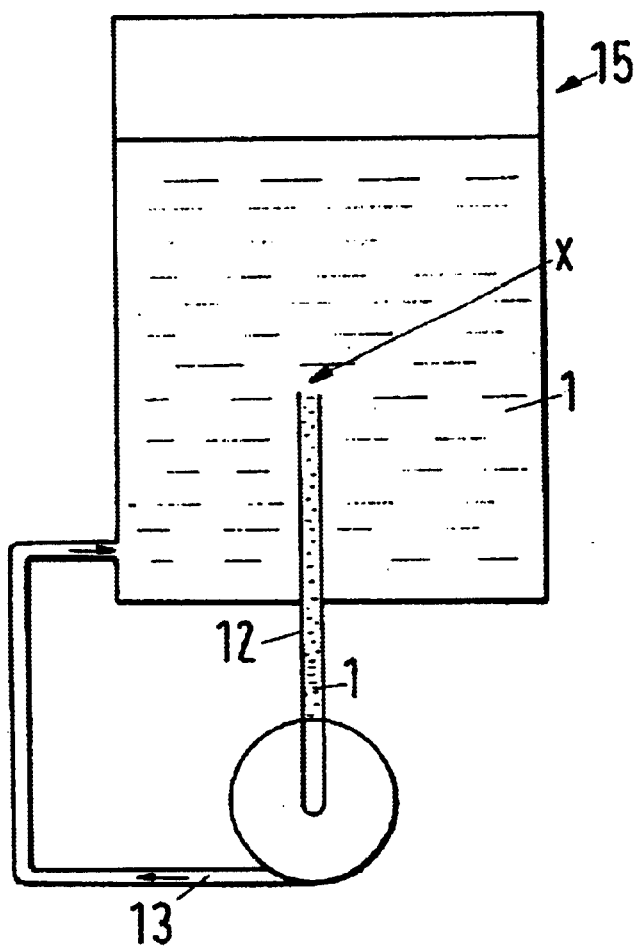
FIG. 10 schematically shows an arrangement for measuring the viscosity in a vessel with fluid.
Figure 11:
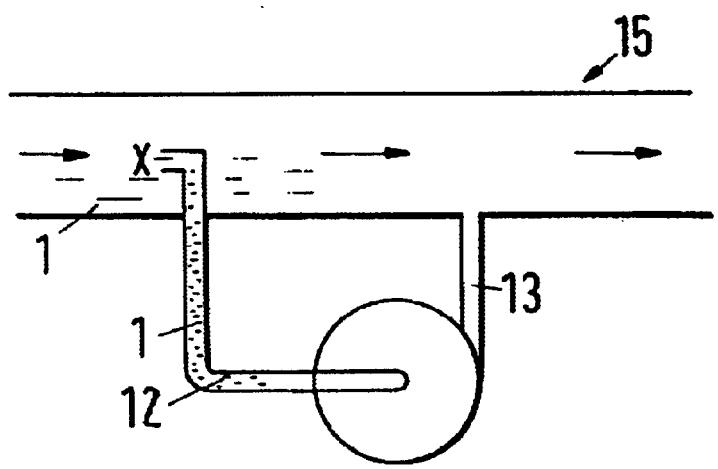
FIG. 11 shows an arrangement for measuring the viscosity in a vessel through which a fluid flows.

The embodiments of the apparatus in accordance with the invention shown schematically in FIGS. 7 and 7a for determining the viscosity η have proved to be particularly advantageous if, as shown in FIGS. 10 and 11, the viscosity η of the fluid 1 should be determined, for example, successively, in a pre-settable time sequence, at different locations X within a vessel 15 containing the fluid 1. The vessel 15 can be designed, for example, as a storage container, as shown in FIG. 10, or also as a line, as sketched in FIG. 11, or differently in another shape. The vessel 15 shown in FIG. 10 can, for example, be a reaction vessel in which a fluid 1 is located which passes through a slow chemical reaction in the course of which the viscosity η alters temporally and/or spatially. The inflow 12 can be designed, for example, as a displaceable feeder which can be displaced to different locations inside the vessel 15 so that the course of the chemical reaction can be observed in temporal and spatial resolution by determining the viscosity η. In this connection, in addition to chemical processes, physical processes can naturally also be observed such as the mixing of a multicomponent fluid 1 or similar processes. For instance, the viscosity η can depend on the location X inside the tube, for example due to deposition processes or due to other circumstances in a tube through which a fluid 1 flows, as shown in FIG. 11. The viscosity η in a flowing fluid is also possible in a flowing fluid 1 in dependence on the location and/or the time via the inflow 12 which can here also be designed as a displaceable feeder. The apparatus in accordance with the invention can naturally, as already stated, also simultaneously supply a hydraulic pump power and so, for example in the embodiment shown in FIG. 10, can additionally support the mixing in the vessel 15.

In this connection, the viscosity η can also be measured continuously at one or more locations X inside the vessel 15. The instantaneous value of the viscosity η determined in this manner can then serve for the control and/or regulation of a chemical or physical process by means of additional mechanical and/or electrical devices (not shown). For example, the delivery of substances, which participate in a chemical or physical process, or also the adjustment of process parameters such as the temperature T, can thus take place in dependence on the viscosity η.

As already mentioned, the internal friction $F_R$ of a fluid 1 generally also depends, in addition to the viscosity η, on the thermodynamic state parameters such as the pressure and temperature T and is furthermore a function of further physical characteristics, in particular of the density of the fluid 1. A possibility of determining the density of a fluid 1 with the aid of the apparatus in accordance with the invention consists of the rotational body 5 being rotated not at a fixed speed ω in the fluid 1, but of the speed ω and/or the torque forming current $I_q$ being varied in accordance with a pre-settable scheme. With a given temperature and a known viscosity, the variation of the internal friction $F_R$ substantially depends only on the density of the fluid 1 with a changing speed ω of the rotational body 5 with a known moment of inertia of the rotational body 5. The reason for this lies in the fact that, when the speed ω of the rotational body 5 rotating in the fluid 1 is changed, the liquid layers, i.e. their masses, coupled to the rotational body 5 by the internal friction $F_R$ have to be accelerated. The time changes in the speed ω are in this connection naturally in a biunique ratio to the corresponding changes in the torque forming current $I_q$.

Figure 12:
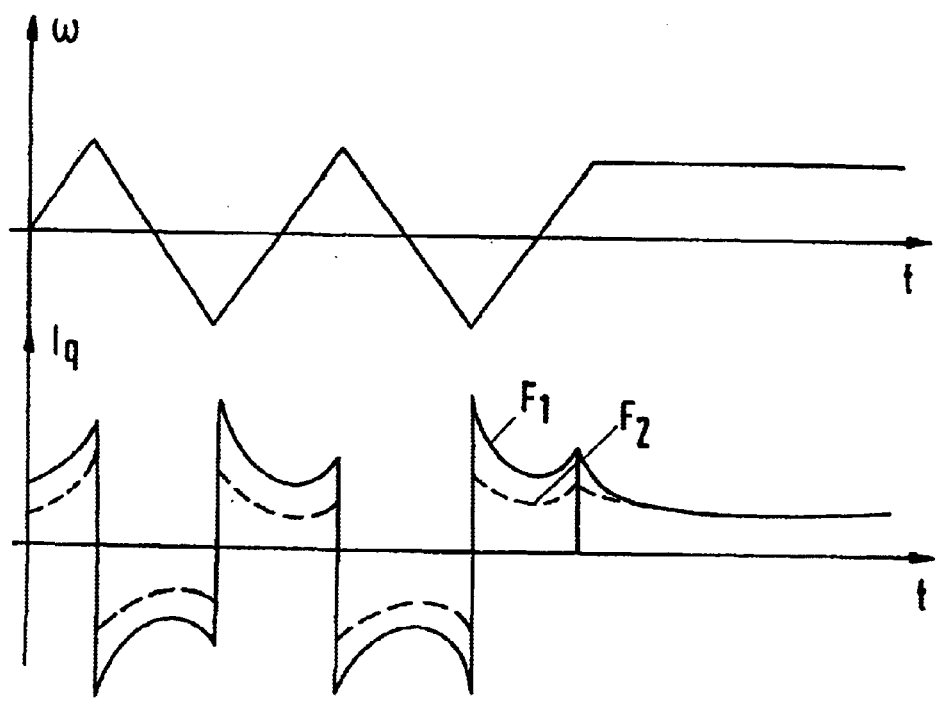
FIG. 12 shows the time dependence of the torque forming current with a preset rotational frequency of the rotational body.

Two basic variants of a method for determining the density of a fluid 1 with the apparatus in accordance with the invention will be described in the following with respect to FIGS. 12 and 13. After the viscosity η has been determined in a first process step not shown in FIG. 12 and FIG. 13, the speed ω of the rotational body 5 is varied in accordance with a pre-settable scheme by a suitable control or regulation (not shown). In FIG. 12, the speed ω is varied in accordance with a sawtooth function as function of time t. The variation can naturally also take place in accordance with any other periodic or non-periodic pre-settable scheme. For example, the speed ω of the rotational body 5 can follow a sinusoid course or the course of a square function, or the rotation can take place, for example, in impulse form. The speed ω can naturally also be kept constant. If the speed ω is pre-set, a corresponding torque forming current $I_q$ is biuniquely connected thereto from whose time-dependent course the density of the fluid 1 can be determined. In the upper part of the diagram shown in FIG. 12, the rotational frequency ω of the rotational body 5 is entered as a function of the time t. The lower part of the diagram schematically shows the course $F_1$ and $F_2$ of the associated torque forming current $I_q$ for two fluids 1 of different density. In this connection, the course $F_1$ is associated with a fluid 1 having a higher density, while the course $F_2$ in contrast characterizes a fluid 1 having a lower density.

Figure 13:
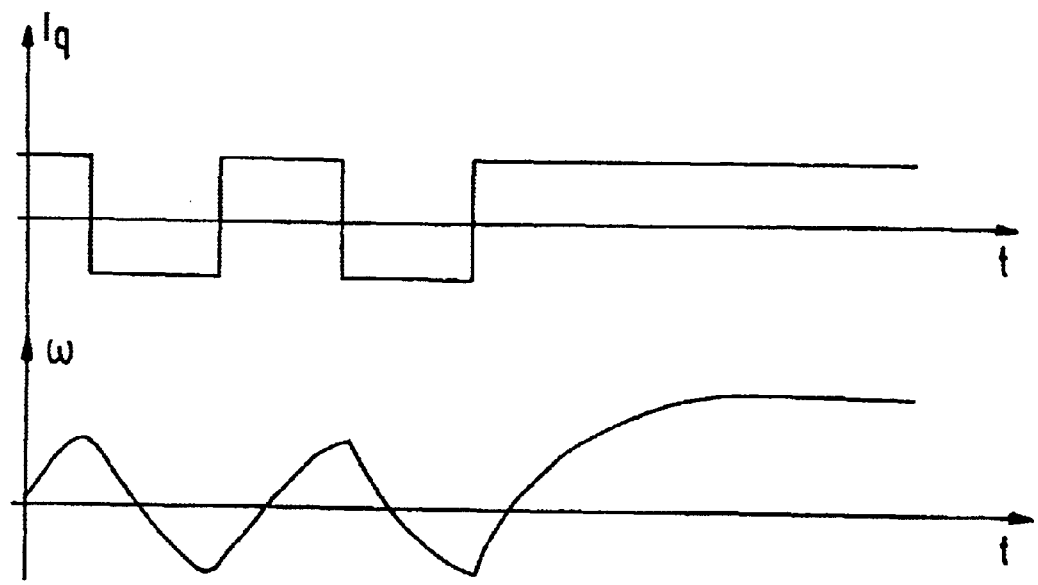
FIG. 13 shows the time dependence of the rotational frequency of the rotational body with a given torque forming current.

In a further variant, the course of the torque forming current $I_q$ is pre-set by a control or regulation (not shown), said course being able, as shown in the upper part of the diagram in FIG. 13, for example, to take a rectangular course as a function of the time t. The torque forming current $I_q$ can naturally also have any other function of time. In particular, the torque forming current $I_q$ can also be kept constant. In this variant of the method in accordance with the invention, the density of the fluid 1 is determined from the resulting time course of the speed ω of the rotational body 5 which is sketched schematically in the lower part of the diagram in FIG. 13.

In accordance with the invention, an apparatus and a method are therefore proposed for determining the viscosity η of a fluid 1 which include an electrical rotary drive 2 having a rotational body 5 rotatable in the fluid 1. In this connection, it is important for the invention that the rotational body 5, which is designed as a rotor 5 of the rotary drive 2, is magnetically journalled through a housing section comprising the rotor 5 in a contact-free manner with respect to the stator 3. The viscosity η is in this connection preferably determined from the rotary drive 2 or the torque forming current $I_q$ linked thereto.

The proposed apparatus in accordance with the invention and the proposed method in this connection show substantial advantages and improvements in comparison with the prior art. Since the rotational body 5 is supported in a completely contact-free manner, the rotary drive 2 has no bearings or drive elements at all which require complex seals or similar devices. The apparatus in accordance with the invention is thus exceptionally suitable, on the one hand, when chemically or physically aggressive fluids 1 have to be examined which are known to attack seals and bearings in particular and which can be permanently damaging. The spectrum of possible application areas is thus considerably expanded with respect to the prior art. Furthermore, the apparatus in accordance with the invention is largely maintenance-free; the maintenance intervals can at least be considerably extended, which ultimately results in an increase in reliability and economic viability of the proposed apparatus with respect to known viscosimeters.

Figure 14:
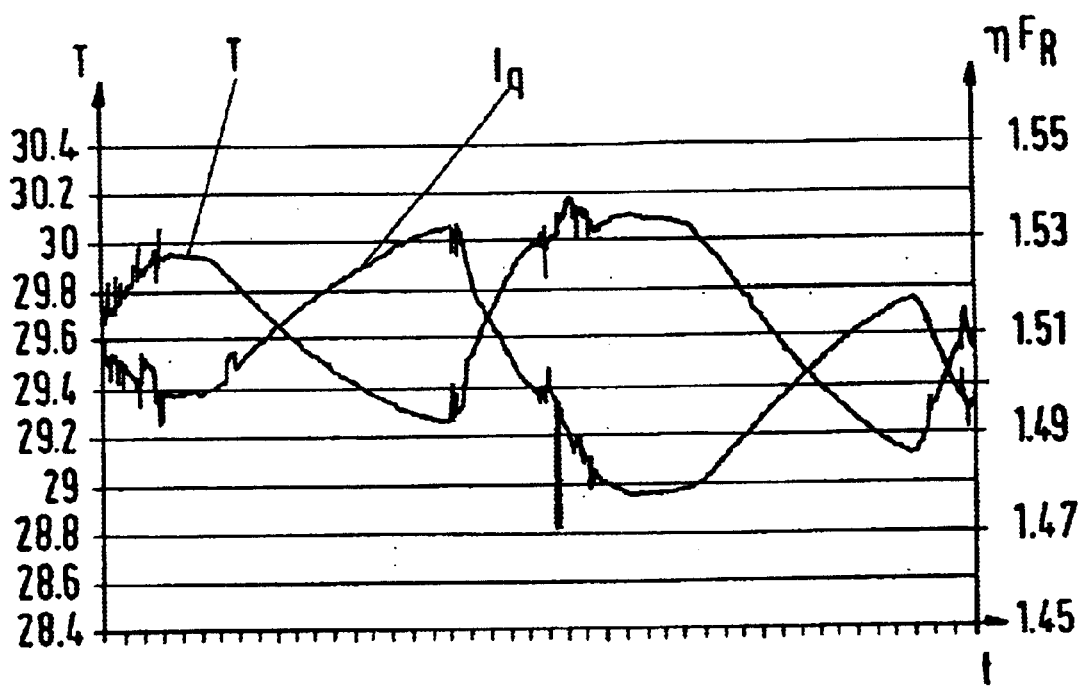
FIG. 14 is a diagram of the temperature dependence of the viscosity $\eta$.

A particular advantage consists of the extremely high sensitivity of the apparatus in accordance with the invention in the determination of the viscosity η. Since the rotational body 5 is supported in a completely contact-free manner, no additional friction losses, e.g. due to bearing friction, have to be taken into account in determining the viscosity η of the fluid 1. The torque forming current $I_q$ thus directly forms a measure for the internal friction $F_R$ of the fluid 1. This means that friction losses can also still be detected in the fluid 1 which are comparable to or smaller than the usually unavoidably occurring friction losses in conventional viscosimeters. The extremely high measuring accuracy of the apparatus in accordance with the invention is impressively demonstrated by FIG. 14. The curve $T_F$ shows the course of the temperature T of a fluid 1 as a function of the time t. The temperature T is entered on the left-hand ordinate of the diagram in FIG. 14. The curve $I_q$ shows the course of the associated torque forming current $I_q$ and the right-hand ordinate of the diagram the viscosity η of the fluid 1 determined therefrom and given in centipoise. As the diagram clearly shows, the apparatus in accordance with the invention easily allows measuring accuracies in the range of a tenth of a percent and better.

The apparatus in accordance with the invention, however, not only allows the determination of the viscosity η of a fluid 1, but, in a particular embodiment, at the same time also allows the fluid 1 to be moderated by means of a heating current which can be fed into the stator winding 4 or can be used additionally as a pump apparatus. The method in accordance with the invention moreover makes it possible also to determine further physical characteristics of the fluid 1, such as its density, by a variation of the torque forming current $I_q$ and/or of the speed ω of the rotational body 5. The apparatus in accordance with the invention for determining the viscosity of a fluid 1 can thus ultimately even be used as a universally usable regulating unit for the control or regulation of quite different physical or chemical processes.

What is claimed is:

1. A method for determining the viscosity of a fluid comprising providing a rotatable body and an electric drive for rotating the body; magnetically rotatably supporting the body in a contact-free manner; immersing the body in the fluid; independently directing electric power to the electric drive for rotating the body and for magnetically supporting the body, respectively; measuring the electric power consumed by the electric drive for rotating the body; and determining the viscosity of the fluid from the electric power consumed by the electric drive for rotating the body.

2. A method according to claim 1 wherein the rotatable body is adapted to induce a flow of the fluid and the electric power consumed by the electric drive is a combination of electric power consumed by the electric drive as a result of the viscosity of the fluid in which the body is immersed and electric power consumed by the electric drive for inducing the flow of the liquid.

3. A method according to claim 2 wherein the electric power consumed by the electric drive as a result of the viscosity of the liquid amounts to at least about 80% of the total electric power consumed by the electric drive.

4. A method according to claim 2 wherein the electric power consumed by the electric drive for overcoming the viscosity of the fluid is at least about 95% of the overall power consumed by the electric drive.

5. A method according to claim 1 wherein the electric drive includes a stator winding for rotating the body and wherein determining the viscosity of the fluid includes varying an electric current directed to the stator winding in accordance with a pre-settable scheme for determining the viscosity of the fluid.

6. A method according to claim 1 including varying a speed of rotation of the rotary drive in accordance with a pre-settable scheme for determining the viscosity of the fluid.

7. A method according to claim 1 wherein the electric drive includes a stator winding, and including regulating a temperature of the fluid in which the rotatable body is immersed by varying a heating current applied to the stator winding.

8. A method according to claim 1 including determining a density of the fluid.

9. A method according to claim 8 wherein at least one of the determining steps is performed as a function of at least one of a location within the fluid and time.

10. Apparatus for determining the viscosity of a fluid comprising a rotatable body for rotation when immersed in the fluid; an electric drive including a stator winding for rotating the body and magnetically rotatably journalling the body in a contact-free manner; a source of electric power for the electric drive for rotating the body; and a processor for determining the viscosity of the fluid from the electric power consumed by the electric drive for rotating the body when the body is immersed and rotates in the fluid.

11. Apparatus according to claim 10 wherein the body includes a fluid flow inducing member that rotates with the rotor and causes at least a portion of the fluid to flow.

12. Apparatus according to claim 11 wherein the body is configured so that at least 95% of the electric power consumed by the electric drive for rotating the body is consumed for overcoming rotational resistance encountered by the body as a result of the viscosity of the fluid.

13. Apparatus according to claim 10 wherein the body and the stator winding define a bearing-free electric motor.

14. Apparatus according to claim 10 including a housing surrounding the rotatable body and separating the body from the stator.

15. Apparatus according to claim 10 wherein the rotatable body has a diameter and a height extending in an axial direction, and wherein the diameter of the body is larger than the height of the body.

16. Apparatus according to claim 10 wherein the electric drive comprises a temple motor and the stator winding is defined by a plurality of L-shaped stator teeth each having first and second transverse limbs connected by a magnetic return yoke, the first stator limb extending parallel to an axis of rotation of the body and the second limb extending radially relative to the axis of rotation, and wherein the stator winding for each tooth is arranged on a relatively longer limb of the tooth.

17. Apparatus according to claim 10 wherein the rotatable body comprises a permanent magnet.

18. Apparatus according to claim 10 including a housing at least partially surrounding the rotatable body.

19. Apparatus according to claim 18 wherein the housing includes heat insulation.

20. Apparatus according to claim 10 wherein the rotatable body includes aids for causing the fluid to flow.

21. Apparatus according to claim 10 including heat insulation for the stator winding.

22. Apparatus according to claims 10 including a temperature sensor for determining a temperature of the fluid.

23. Apparatus according to claim 10 wherein the rotatable body is configured to substantially prevent the body from causing fluid to flow when the body rotates and is immersed in fluid.

24. Apparatus according to claim 10 including a housing within which the rotatable body rotates, the housing including an inlet and an outlet permitting fluid flow through the housing.

25. Apparatus according to claim 24 wherein the rotatable body includes pumping aids inducing fluid flow through the housing from the inlet to the outlet when the body rotates.

26. A method for determining the viscosity of a fluid comprising providing a rotatable body and an electric drive including a stator winding for rotating the body; magnetically rotatably supporting the body in a contact-free manner with respect to the stator winding; immersing the body in the fluid; independently directing electric power to the electric drive for rotating the body and for magnetically supporting the body, respectively; measuring the electric power consumed by the electric drive for rotating the body; with the body inducing at least a portion of the fluid to flow; determining the viscosity of the fluid from the electric power consumed by the electric drive for rotating the body; and maintaining an operating range for the electric drive so that the electric power needed by the body for overcoming a viscous resistance of the fluid amounts to at least about 80% of the total electric power consumed by the electric drive.

27. Apparatus for determining the viscosity of a fluid comprising a rotatable body for rotation when immersed in the fluid and causing at least a portion of the fluid to flow; an electric drive including a stator winding for rotating the body and magnetically rotatably journalling the body in a contact-free manner relative to the stator winding; a source of electric power for the electric drive for rotating the body; the electric drive and the body being configured so that electric power needed by the body to overcome viscous resistance of the fluid amounts to at least about 80% of the total power consumed by the electric drive; and a processor for determining the viscosity of the fluid from the electric power consumed by the electric drive for rotating the body when the body is immersed and rotates in the fluid.

* * * * *